United States Patent [19]

Okamoto et al.

[11] Patent Number: 5,846,940
[45] Date of Patent: Dec. 8, 1998

[54] CORNEAL THERAPEUTIC AGENT

[75] Inventors: Sinseiro Okamoto, 31-19, O-okayama 1-chome, Meguro-ku, Tokyo 152; Sakae Amagaya, Tsukuba; Kenji Sakamoto, Akita-ken; Masanao Kanitani, Ibaraki-ken, all of Japan

[73] Assignee: Sinseiro Okamoto, Japan

[21] Appl. No.: 776,613

[22] PCT Filed: Aug. 4, 1995

[86] PCT No.: PCT/JP95/01549

§ 371 Date: Feb. 3, 1997

§ 102(e) Date: Feb. 3, 1997

[87] PCT Pub. No.: WO96/04002

PCT Pub. Date: Feb. 15, 1996

[30] Foreign Application Priority Data

Aug. 5, 1994 [JP] Japan ..................... 6-184844

[51] Int. Cl.$^6$ .................................................. A61K 38/08
[52] U.S. Cl. ........................... 514/17; 514/912; 514/914; 530/325
[58] Field of Search ............ 514/17, 912, 914; 530/399, 329; 426/427

[56] References Cited

U.S. PATENT DOCUMENTS

| | | | |
|---|---|---|---|
| 5,145,680 | 9/1992 | Hayashi | 424/427 |
| 5,348,939 | 9/1994 | Horowitz et al. | 514/8 |
| 5,360,611 | 11/1994 | Robertson et al. | 424/427 |
| 5,360,789 | 11/1994 | Nakao et al. | 514/12 |
| 5,374,612 | 12/1994 | Ito et al. | 505/232 |
| 5,374,621 | 12/1994 | Wei | 514/14 |
| 5,393,740 | 2/1995 | Amagaya et al. | 514/17 |

FOREIGN PATENT DOCUMENTS

| | | |
|---|---|---|
| 0 140 998 | 5/1985 | European Pat. Off. . |
| 0 333 071 | 3/1988 | European Pat. Off. . |
| 0 339 905 | 11/1989 | European Pat. Off. . |
| 526192 | 2/1993 | European Pat. Off. . |
| 63-5745 | 8/1988 | Japan . |
| WO 93/06130 | 4/1993 | WIPO . |

*Primary Examiner*—Stephen Walsh
*Assistant Examiner*—Eliane Lazar-Wesley
*Attorney, Agent, or Firm*—Nixon & Vanderhye

[57] ABSTRACT

A corneal therapeutic agent comprises at least one of a hexapeptide and a pharmacologically acceptable salt thereof, represented by formula (I) shown below, and a pharmacologically acceptable carrier, A-B-Pro-C-D-E (I)

where A is L- or D-arginine or lysine whose N-terminal amino group is deaminated, alkylated or acylated; B is L- or D-arginine, lysine or hystidine; Pro is L- or D-proline; C is L- or D-tyrosine, tryptophane, or phenylalanine; D is L- or D-valine, isoleucine, or leucine having an amino group whose hydrogen atom may be substituted with an alkyl group having 1 to 4 carbon atoms; E is L- or D-valine, isoleucine or leucine having a C-terminal carboxylic group which is unsubstituted or substituted with —COOR, —CH$_2$OR or —CONHR, where R represents a hydrogen atom or an alkyl group having 1 to 4 carbon atoms.

5 Claims, No Drawings

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
      ( A ) LENGTH: 6 amino acids
      ( B ) TYPE: amino acid
      ( C ) STRANDEDNESS:
      ( D ) TOPOLOGY: linear ( i i ) MOLECULE TYPE: peptide ( x i ) SEQUENCE DESCRIPTION: SEQ ID NO:1:

Arg Arg Pro Tyr Ile Leu
   1                5

( 2 ) INFORMATION FOR SEQ ID NO:2:

( i ) SEQUENCE CHARACTERISTICS:
      ( A ) LENGTH: 6 amino acids
      ( B ) TYPE: amino acid
      ( C ) STRANDEDNESS:
      ( D ) TOPOLOGY: linear ( i i ) MOLECULE TYPE: peptide ( i x ) FEATURE:
      ( A ) NAME/KEY: Modified-site
      ( B ) LOCATION: 6
      ( D ) OTHER INFORMATION: /product="Leucinol"

( x i ) SEQUENCE DESCRIPTION: SEQ ID NO:2:

Arg Arg Pro Tyr Ile Xaa
   1                5

( 2 ) INFORMATION FOR SEQ ID NO:3:

( i ) SEQUENCE CHARACTERISTICS:
      ( A ) LENGTH: 6 amino acids
      ( B ) TYPE: amino acid
      ( C ) STRANDEDNESS:
      ( D ) TOPOLOGY: linear ( i i ) MOLECULE TYPE: peptide ( x i ) SEQUENCE DESCRIPTION: SEQ ID NO:3:

Arg Lys Pro Tyr Ile Leu
   1                5

( 2 ) INFORMATION FOR SEQ ID NO:4:

( i ) SEQUENCE CHARACTERISTICS:
      ( A ) LENGTH: 6 amino acids
      ( B ) TYPE: amino acid
      ( C ) STRANDEDNESS:
      ( D ) TOPOLOGY: linear ( i i ) MOLECULE TYPE: peptide ( x i ) SEQUENCE DESCRIPTION: SEQ ID NO:4:

Arg Arg Pro Trp Ile Leu
   1                5

( 2 ) INFORMATION FOR SEQ ID NO:5:

( i ) SEQUENCE CHARACTERISTICS:

(A) LENGTH: 6 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:5:

Arg Arg Pro Tyr Ile Leu
1               5

(2) INFORMATION FOR SEQ ID NO:6:

(i) SEQUENCE CHARACTERISTICS:
            (A) LENGTH: 6 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Modified-site
            (B) LOCATION: 6
            (D) OTHER INFORMATION: /product="Leucinol"

(xi) SEQUENCE DESCRIPTION: SEQ ID NO:6:

Arg Arg Pro Tyr Ile Xaa
1               5

(2) INFORMATION FOR SEQ ID NO:7:

(i) SEQUENCE CHARACTERISTICS:
            (A) LENGTH: 6 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:7:

Arg Lys Pro Tyr Ile Leu
1               5

(2) INFORMATION FOR SEQ ID NO:8:

(i) SEQUENCE CHARACTERISTICS:
            (A) LENGTH: 6 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:8:

Arg Arg Pro Trp Ile Leu
1               5

(2) INFORMATION FOR SEQ ID NO:9:

(i) SEQUENCE CHARACTERISTICS:
            (A) LENGTH: 6 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:9:

Arg Arg Pro Tyr Ile Leu
1               5

( 2 ) INFORMATION FOR SEQ ID NO:10:

( i ) SEQUENCE CHARACTERISTICS:
        ( A ) LENGTH: 6 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( A ) NAME/KEY: Modified-site
        ( B ) LOCATION: 6
        ( D ) OTHER INFORMATION: /product="Leucinol"

( x i ) SEQUENCE DESCRIPTION: SEQ ID NO:10:

Arg  Arg  Pro  Tyr  Ile  Xaa
1                       5

( 2 ) INFORMATION FOR SEQ ID NO:11:

( i ) SEQUENCE CHARACTERISTICS:
        ( A ) LENGTH: 6 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:11:

Arg  Lys  Pro  Tyr  Ile  Leu
1                       5

( 2 ) INFORMATION FOR SEQ ID NO:12:

( i ) SEQUENCE CHARACTERISTICS:
        ( A ) LENGTH: 6 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:12:

Arg  Arg  Pro  Trp  Ile  Leu
1                       5

( 2 ) INFORMATION FOR SEQ ID NO:13:

( i ) SEQUENCE CHARACTERISTICS:
        ( A ) LENGTH: 6 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /product="Arg or Lys"

( i x ) FEATURE:
        ( A ) NAME/KEY: Modified-site
        ( B ) LOCATION: 2
        ( D ) OTHER INFORMATION: /product="Arg, Lys or His"

( i x ) FEATURE:
        ( A ) NAME/KEY: Modified-site
        ( B ) LOCATION: 4
        ( D ) OTHER INFORMATION: /product="Tyr, Trp or Phe"

( i x ) FEATURE:
  ( A ) NAME/KEY: Modified-site
  ( B ) LOCATION: 5
  ( D ) OTHER INFORMATION: /product="Val, Ile or Leu"

( i x ) FEATURE:
  ( A ) NAME/KEY: Modified-site
  ( B ) LOCATION: 6
  ( D ) OTHER INFORMATION: /product="Val, Ile or Leu"

( x i ) SEQUENCE DESCRIPTION: SEQ ID NO:13:

Xaa  Xaa  Pro  Xaa  Xaa  Xaa
1                 5

CORNEAL THERAPEUTIC AGENT

This application is the U.S. National stage of PCT/JP95/01549 filed Aug. 4, 1995.

TECHNICAL FIELD

The present invention relates to a corneal therapeutic agent, and more particularly, to a corneal therapeutic agent which accelerates the healing of the cornea after photon rendering keratectomy using an ultraviolet laser, especially, an excimer laser, and which prevents corneal opacity.

BACKGROUND ART

In the ophthalmic field, it has been recently studied to cure paropsia by geometrical incision of an eye. The corneal incision is employed to cure, for example, ametropia such as myopia, hyperopia, and astigmatism and corneal disorders such as corneal opacity. The surgical treatment mentioned above is quite advantageous in respect that the permanent correction can be realized, compared to conventional eyesight-correction methods using compensating lenses such as glasses or contact lenses.

As a representative example of the surgical treatment for paropsia, there is a myopia therapy by means of keratectomy. In particular, radial keratotomy, one of the surgical treatment methods for ametropia, is used for correcting myopia caused by excessive corneal arcuation. In this method, cutting is made along the radial lines extending outwardly from a center of the cornea, usually with a surgical knife. The depth of the cutting is generally about 90 to 95% of the cornea thickness. The number of the cutting lines is possibly in the range of 4–16, generally, 8–12. The corneal incision mentioned above makes the cornea relaxed and slightly flattened, thereby mitigating or overcoming the myopia.

Besides this, photon rendering keratectomy (PRK) using an excimer laser is known. In the PRK method, the central portion of a corneal front face is cut off to form a depressed portion. The cornea is cut off in the form of a meniscus. In an infrared laser such as a carbonate gas laser or a YAG laser, molecules constituting an irradiated object absorb a laser beam, causing molecular vibration. Heat generated by the molecular vibration melts and cuts the object. In the excimer laser, however, photon energy cuts the bonds of the molecules constituting the irradiated object. As a result, the cornea is rarely denatured with heat. In addition, the laser can process the object precisely, so that only required region of the cornea can be cut off accurately to a necessary depth.

However, if the cornea is not completely cured after any surgery, the phenomena called white corneal opacity, namely keratoleukoma, will occur in some cases. The keratoleukoma is caused by random secretion of collagen to the corneal surface during a wound-healing stage. The random collagen secretion is induced by the stimulation of the cornea with an excimer laser or the like during a surgical operation.

DISCLOSURE OF THE INVENTION

It is an object of the present invention to provide a corneal therapeutic agent capable of preventing keratoleukoma by accelerating the curing of a cornea after the surgical operation of ametropia.

The present invention provides a corneal therapeutic agent comprising at least one of a hexapeptide and a pharmacologically acceptable salt thereof (hereinafter, referred to as "HP") represented by formula (I) shown below, and a pharmacologically acceptable carrier, $$A\text{-}B\text{-}Pro\text{-}C\text{-}D\text{-}E \tag{I}$$

where A is L- or D-arginine or lysine whose N-terminal amino group is deaminated, alkylated or acylated; B is L- or D-arginine, lysine or hystidine; Pro is L- or D-proline; C is L- or D-tyrosine, tryptophane, or phenylalanine; D is L- or D-valine, isoleucine, or leucine having an amino group whose hydrogen atom may be substituted with an alkyl group having 1 to 4 carbon atoms; E is L- or D-valine, isoleucine or leucine having a C-terminal carboxylic group which is unsubstituted or substituted with —COOR, —CH$_2$OR or —CONHR, where R represents a hydrogen atom or an alkyl group having 1 to 4 carbon atoms.

The corneal therapeutic agent is developed for curing a corneal wound and preventing corneal opacity, i.e., keratoleukoma, and is used in these uses.

The corneal therapeutic agent may further contain at least one of an epithelial cell growth factor (hereinafter, referred to as "EGF") and fibronectin (hereinafter, referred to as "FN"), as an active ingredient. In this case, a more excellent effect can be expected.

It is another object of the present invention to provide a corneal therapeutic kit comprising Agent A containing HP and Agent B containing at least one of EGF and FN. The agent A and the agent B may be administered separately or simultaneously.

It is still another object of the present invention to provide a corneal therapeutic kit comprising Agent A containing HP, Agent B containing EGF, and Agent C containing FN. The Agents A, B, and C may be administered separately or simultaneously.

BEST MODE OF CARRYING OUT THE INVENTION

Hereinbelow, the present invention will be described in detail.

Amino acids described in the specification will be abbreviated according to the IUPAC-IUB biochemical nomenclature (CBN). The amino acids are expressed as follows:

Arg: L-arginine
Ile: L-isoleucine
Lys: L-lysine
Pro: L-proline
Trp: L-tryptophan
D-Arg: D-arginine
D-Ile: D-isoleucine
D-Lys: D-lysine
D-Pro: D-proline
D-Trp: D-tryptophan
His: L-histidine
Leu: L-leucine
Phe: phenylalanine
Tyr: L-tyrosine
Val: L-valine
D-His: D-histidine
D-Leu: D-leucine
D-Phe: D-phenylalanine
D-Tyr: D-tyrosine
D-Val: D-valine As six amino acids constituting HP, either D- or L-amino acids may be used.

The active agent HP of the corneal therapeutic agent of the present invention has been already proposed as a novel hexapeptide by the applicants of the present invention (Jpn. Pat. Appln. KOKAI Publication No. 5-194590).

In formula (I), the first amino acid A of the N-terminal of the hexapeptide is arginine or lysine whose N-terminal amino group is deaminated, alkylated, or acylated.

The deamination of the N-terminal amino group, for example, arginine, is achieved by dissolving 5-amino valeric acid in 2N aqueous sodium hydroxide solution and then adding S-methylthiocarbamide thereto.

Examples of the alkyl group introduced into the N-terminal amino group of amino acid A are methyl, ethyl, propyl, and butyl. The alkylation of the N-terminal amino group can be carried out by reacting amino acid A with the corresponding alkylbromide, such as methyl bromide or ethyl bromide, in an organic solvent such as methylene chloride or pyridine.

Examples of the acyl group introduced into the N-terminal amino group of amino acid A are formyl, acetyl, propionyl, benzoyl, and p-toluenesulfonyl.

The acylation of the N-terminal amino group can be performed by reacting amino acid A with an acid anhydride such as acetic anhydride, or an acid chloride such as acetyl chloride, in an organic solvent such as methylene chloride or pyridine.

In formula (I), the peptide bond between fourth amino acid C and fifth amino acid D from the N-terminal of the hexapeptide is represented by formula (II) shown below.

$$—CO—NX— \quad (II)$$

where X is hydrogen atom or a $C_1$ to $C_4$- alkyl group.

In formula (II), the $C_1$ to $C_4$- alkyl group is, for example, methyl, ethyl, n-propyl, t-propyl, n-butyl, i-butyl, or t-butyl.

In formula (I), amino acid E, the sixth amino acid from the N-terminal of the hexapeptide, is valine, leucine or isoleucine. The C-terminal carboxyl group of sixth amino acid E may be substituted or unsubstituted with —COOR, —$CH_2$OR, or —CONHR, where R is a hydrogen atom or an alkyl group having 1 to 4 carbon atoms. Examples of the alkyl group are methyl, ethyl, n-propyl, t-propyl, n-butyl, i-butyl, or t-butyl.

More specific examples of the aforementioned HP following hexapeptides No. 1 to 12.

| Peptide No. | Sequence |
|---|---|
| 1 | Desamino-Arg—Arg—Pro—Tyr—Ile—Leu—OH |
| 2 | Desamino-Arg—Arg—Pro—Tyr—Ile-Leucinol |
| 3 | Desamino-Arg—Lys—Pro—Tyr—Ile—Leu—$NH_2$ |
| 4 | Desamino-Arg—Arg—Pro—Trp—Ile—Leu—OEt |
| 5 | N—acetyl—Arg—Arg—Pro—Tyr—Ile—Leu—OH |
| 6 | N—acetyl—Arg—Arg—Pro—Tyr—Ile-Leucinol |
| 7 | N—acetyl—Arg—Lys—Pro—Tyr—Ile—Leu—$NH_2$ |
| 8 | N—actyl—Arg—Arg—Pro—Trp—Ile—Leu—OEt |
| 9 | N—butyl—Arg—Arg—Pro—Tyr—Ile—Leu—OH |
| 10 | N—butyl—Arg—Arg—Pro—Tyr—Ile-Leucinol |
| 11 | N—butyl—Arg—Lys—Pro—Tyr—Ile—Leu—$NH_2$ |
| 12 | N—butyl—Arg—Arg—Pro—Trp—Ile—Leu—OEt |

The aforementioned HP can be synthesized by either a conventionally-known liquid-phase synthesizing method or a solid-phase synthesizing method which is generally employed for peptide synthesis. The details of the solid-phase HP synthesizing method are described in Jpn. Pat. Appln. KOKAI Publication No. 5-194590.

The active agent of the corneal therapeutic agent of the present invention also includes salts of HP. Examples of pharmacologically acceptable nonpoisonous salts include a salt of HP with an alkaline metal such as sodium or potassium; an alkaline earth metal such as calcium or magnesium; an acid-added salt such as a salt of an inorganic acid including hydrochloric acid, sulfuric acid, phosphoric acid, or carbonic acid; and an acid-added salt such as a salt of an organic acid including acetic acid, propionic acid, tartaric acid, succinic acid, malic acid, aspartic acid, or glutamic acid.

The corneal therapeutic agent of the present invention may be used as ophthalmic local preparations. Examples of the ophthalmic local preparations are eye perfusion liquids, eye drops, eye ointments and the like. The corneal therapeutic agent of the present invention for use in the eye perfusion liquid can be prepared by dissolving HP in sterilized and purified water. In order to make the composition of the eye perfusion liquid closer to that of aqueous humor, pharmacologically acceptable additives such as an isotonizing agent and a buffer can be added as necessary. Examples of the additives include glucose, sodium chloride, potassium chloride, calcium chloride, magnesium sulfate, sodium bicarbonate, glutathion, and the like.

The corneal therapeutic agents of the present invention used as an eye drop include an aqueous eye drop, a non-aqueous eye drop, an opthalmic suspension, and an opthalmic emulsion. The eye drop is prepared by dissolving or suspending HP in an aqueous solvent such as sterilized and purified water or saline; or in a non-aqueous solvent, for example, a vegetable oil such as cotton seed oil, soybean oil, sesame oil, or peanut oil. In this case, pharmacologically acceptable additives such as an isotonizing agent, pH controlling agent, viscosity improver, suspending agent, emulsifying agent, and preservative may be added as necessary. Specific examples of the isotonizing agent includes sodium chloride, boric acid, sodium nitride, potassium nitride, D-mannitol, glucose, and the like. Examples of the pH controlling agent include boric acid, sodium sulfite anhydride, hydrochloric acid, citric acid, sodium citrate, acetic acid, potassium acetate, sodium carbonate, borax, and the like. Examples of the viscosity improver include methyl cellulose, hydroxypropyl cellulose, polyvinyl alcohol, sodium chondroitin sulfate, polyvinylpyrrolidone, and the like. Examples of the suspending agent are polysorbate 80, polyoxyethylene hardened castor oil 60, polyoxy hardened castor oil, and the like. Examples of the emulsifying agent are egg-yolk lecithin, polysorbate 80, and the like. Examples of the preservative include benzalkonium chloride, benzetonium chloride, chlorobutanole, phenylethyl alcohol, paraoxy benzoate, and the like.

The corneal therapeutic agent of the present invention for the eye drop contains HP in the range of 10 ng/ml to 100 $\mu$g/ml. The eye drop is administered 1 to 6 times per day and applied 1 to 3 droplets per time.

An eye ointment is also included in the corneal therapeutic agent of the present invention. The corneal therapeutic agent of the present invention used as the eye ointment can be appropriately prepared by employing a base material generally used in an eye ointment.

The corneal therapeutic agent for the eye ointment contains HP in the range of 10 ng/ml to 100 $\mu$g/ml. The eye ointment may be applied to the rear side of an eye lid by means of an eye-drop stick 1 to 6 times per day and 100 $\mu$g per time.

The corneal therapeutic agent of the present invention can be applied by attaching it onto contact lenses. In this case, the holding period of the agent is increased, improving the efficacy thereof.

The corneal therapeutic agent of the present invention mentioned above, accelerates healing of a corneal wound given bye, e.g., an ametropia operation and shortens the time required for the recovery of the cornea after the operation by virtue of the corneal wound-healing accelerating effect. Furthermore, the corneal therapeutic agent of the present invention has a corneal-opacity preventing effect, so that corneal opacity, i.e., keratoleukoma, can be cured and prevented.

In the radial keratotomy, the cornea is cut with a surgical knife to form a dissected portion having a V-shape cross section extending from the epithelium to the parenchyma via the Bowman's membrane, viewing from the surface side of the cornea. It takes several days to cure the dissection after the surgery. In the initial stage, the epithelial cells are grown along the surface of the dissected wall downwardly from the epithelium, covering the entire wall surface of the dissected portion. Then, the parenchymatous tissue is regenerated at the bottom of the dissected portion. As the parenchymatous tissue is healed from the bottom of the dissected portion upwardly as mentioned above, the epithelial cells, which have been formed on the wall of the dissected portion in the initial stage, are gradually protruded upward.

However, the portion which has been formed of the parenchymatous tissue before the surgical operation is not regenerated completely only by the parenchymatous tissue and partly recouped by the epithelial cells formed at the initial stage of the healing step. Therefore, the cornea after the surgical operation is not completely recovered and does not regain the normal condition. Since the cornea is not completely healed, the cornea is mechanically weakened, generating keratoleukoma in some cases.

In contrast, in the PRK method using an excimer laser, the corneal epithelium is cut off with a surgical knife, and thereafter, the corneal parenchymatous layer is cut off by an excimer laser. Hence, only the surface portion of the parenchymatous tissue can be cut off. In this manner, the wound due to the surgical operation can be healed only in the initial epithelial cell formation stage. As a result, the portion cut off by the excimer laser in the surgical operation is covered by the epithelial cells, thereby regaining almost the normal and healthy condition. However, the epithelial cells of the healed cornea are sometimes nonuniformly formed, so that the surface of the corneal epithelium becomes rough. In addition, when the recovery of the epithelial cells is delayed, keratoleukoma may be developed even after the PRK surgery, similarly to the case of the radial keratotomy.

In the foregoing, the PRK method using an excimer laser has been explained. In the PRK method, an ultraviolet laser other than an excimer laser can be used. The ultraviolet laser is referred to a laser having a wavelength within the ultraviolet range of about 1 to 400 nm.

When the corneal therapeutic agent of the present invention is applied to the cornea after the radial keratotomy or the PRK surgery, the healing of the surgical wound can be accelerated while inflammation of the surgical dissection and the cut-off portion and the secretion of collagen are being suppressed. Therefore, keratoleukoma is prevented.

As the active gradient of the corneal therapeutic agent of the present invention, HP may be used alone or in combination with a conventionally-known compound having a corneal therapeutic activity. For example, the corneal therapeutic agent of the present invention may contain an epithelium growth factor (hereinafter, referred to as "EGF") which is disclosed in Jpn. Pat. Appln. KOKAI Publication Nos. 63-5745 and 59-65020, and may contain fibronectin described in Jpn. Pat. Appln. KOKAI Publication No. 63-5745. In this case, more excellent corneal healing effect can be attained.

Alternatively, both Agent A containing HP and Agent B containing either EGF or FN are prepared and administered separately or simultaneously. Agents A and B, each containing an active agent are applied, for example in the form of ophthalmic local preparations such as an eye drop or an eye ointment. Agents A and B may be administered separately or simultaneously. The effective amount of EGF used in an eye drop falls within the range of 0.01 to 50 $\mu$g/ml. The effective amount of FN used in an eye drop falls within the range of 10 ng/ml to 1 mg/ml.

Similarly, Agent A containing HP, Agent B containing EGF, and Agent C containing FN are prepared and also administered separately or simultaneously.

When HP, EGF, and FN are used together as mentioned above, the initial stage of the corneal healing is accelerated by EGF having an epithelial regeneration growth activity. In addition, FN has a activity concerning an intercellular adhesiveness. Hence, the cornea healing activity of HP can be accelerated by EGF and FN. As a result, keratoleukoma can be prevented and the cornea can be recovered quickly.

EXAMPLES

Hereinbelow, examples of the present invention will be described in detail.

The following tests were performed with respect to the accelerating activity for the corneal wound healing after excimer laser treatment.

1. Sample Preparation

The following substances were used in this test.

HP 1: N-acetyl-Arg-Arg-Pro-Tyr-Ile-Leucinol

HP 2: N-acetyl-Arg-Arg-Pro-Tyr-Ile-Leu-OH

EGF: manufactured by Bio Medical Technologies

FN: manufactured by Bio Medical Technologies

HP 1 and HP 2 were synthesized in accordance with Examples 31 and 32 described in Jpn. Pat. Appln. KOKAI Publication No. 5-194590.

HP 1 and HP 2 were diluted with 1.2 ml of an oxyglutathion eye-perfusion/washing solution (trade name: BSS plus, manufactured by Santen Seiyaku) to obtain a diluted solution in a final concentration of 0.1 mg/ml. 1000 $\mu$g/ml of EGF was diluted with 1 ml of the oxyglutathion eye-perfusion/washing solution to obtain a diluted solution in a final concentration of 0.1 mg/ml. FN was diluted with 10 ml of the oxyglutathion eye-perfusion/washing solution to obtain a diluted solution in a final concentration of 0.1 mg/ml.

2. Corneal Incision of Test Animal

A colored rabbit was used as a test animal. The following surgical operation was applied to the rabbit.

An excimer laser was radiated to the corneas of both eyes of the rabbit under the condition of 180 mj/10 nsec (10 Hz) per pulse. By this radiation, the surface of central corneal parenchyma was cut off by abrasion in the form of a meniscus having a diameter of 4.5 mm (9.9 diopter) and a maximum center-depth of 70 $\mu$m. The excimer laser was radiated by using Omunimed (trade name) manufactured by Summit (U.S.A.).

3. Sample Administration

Each of the aforementioned samples was administered to both eyes twice a day. A single droplet (about 50 $\mu$l) was administrated once in the morning and the afternoon for 5 to 7 days.

TABLE 1

| Example | Sample | Conc. (μg/ml) | Number of animals | Number of animal eyes |
|---|---|---|---|---|
| control | no treatment | | 1 | 2 |
| 1 | HP 1 | 100 | 1 | 2 |
| 2 | HP 2 | 100 | 1 | 2 |
| 3 | FN + HP1 | 100 | 1 | 2 |
| 4 | FN + HP2 | 100 | 1 | 2 |
| 5 | EGF + HP1 | 100 | 3 | 6 |
| 6 | EGF + FN HP1 | 100 | 3 | 6 |
| 7 | HP1 + HP2 FN + EGF | 100 | 1 | 2 |

As Comparative examples, eye drops were prepared by dissolving the aforementioned samples in the oxyglutathion eye perfusion/washing solution in accordance with Table 2 and administered to both eyes of the rabbit.

As a control, an excimer laser was radiated to the rabbit, and thereafter, no treatment was provided thereto.

TABLE 2

| Example | Sample | conc. (μg/ml) | Number of animals | Number of animal eyes |
|---|---|---|---|---|
| control | no treatment | | 1 | 2 |
| 1 | FN | 100 | 1 | 2 |
| 2 | EGF | 100 | 1 | 2 |
| 3 | FN + EGF | 100 | 3 | 6 |

After completion of droplet administration, right and left eyes were taken out from the rabbit and fixed with a glutathion aldehyde/formalin fixing solution. After the fixation, each cornea including a laser irradiated portion and a non-irradiated portion were excised out. Then, paraffin blocks were prepared in accordance with a customary method and thin-film slices of 5 μm thick were prepared by means of a microtome. The obtained corneal slices were stained with H.E. (hematoxylin-eosin) and then subjected to special staining such as PAS or trichrome. Thereafter, the slices were observed with an optical microscope.

The observation results are as follows:

In the control, no corneal epithelium regeneration was observed at the center of the excimer-laser irradiated portion.

In the FN group of Comparative Example 1, epithelium regeneration was observed in the entire irradiated portion. However, the thickness of the regenerated epithelium was nonuniform and inflammatory changes were observed mainly ascribed to inflammatory cellular infiltration. In addition, vacuolation and fibroblast growth were relatively significant at a portion immediately under the epithelium.

In the EGF group of Comparative Example 2, epithelium regeneration was observed in the entire irradiated portion. The thickness of the regenerated epithelium is nearly uniform. However, vacuolation and fibroblast growth were observed in the tunica propria under the epithelium. Furthermore, inflammatory changes were observed.

In the FN+EGF group of Comparative Example 3, epithelium regeneration was observed in the entire irradiated portion. However, the thickness of the regenerated epithelium was nonuniform. Vacuolation and fibroblast growth were observed in the tunica propria under the epithelium. In addition, inflammatory changes were observed.

In the HP1 group of Example 1 and the HP2-group of Example 2, the regeneration of the epithelium was observed in the entire irradiated portion. However, the thickness of the regenerated epithelium was nonuniform. Vacuolation and fibroblast growth were observed in the tunica propria. However, inflammatory changes were not observed.

In the FN+HP1 group of Example 3, FN+HP2 group of Example 4, EGF+HP1 group of Example 5, epithelium regeneration was observed in the entire irradiated portion. However, the thickness of the regenerated epithelium was nonuniform. Vacuolation and fibroblast growth were low in the tunica propria. However, inflammatory changes were not observed.

In the EGF+FN+HP1 group of Example 6, epithelium regeneration was observed in the entire irradiated portion. The thickness of the regenerated epithelium was almost uniform. Slight vacuolation were observed under the epithelium. Inflammatory changes were not observed.

In the HP1+HP2+FN+EGF group of Example 7, epithelium regeneration was observed in the entire irradiated portion. The thickness of the regenerated epithelium was normal. Vacuolation and fibroblast growth were rarely observed under the epithelium. Inflammatory changes were not observed.

From the results above, since the cornea was regenerated in the HP1 group of Example 1 and HP2 group of Example 2, the samples of Examples 1 and 2 were confirmed to have an corneal wound healing accelerating effect, as the same as in the FN group of Comparative Example 1 and the EGF group of Comparative Example 2 which are conventionally known as a corneal therapeutic agent. Furthermore, although inflammatory changes were observed in the FN group of Comparative Example 1 and the EGF group of Comparative Example 2, no inflammatory changes were observed in the HP1 group of Example 1 and the HP2 group of Example 2. Hence, it was found that the occurrence of inflammation can be prevented. As a result, it was demonstrate that HP1 and HP2 can be used as a corneal therapeutic agent although the thickness of the regenerated epithelium is nonuniform.

On the other hand, in the case where HP1 or HP2 is used together with FN or EGF, as are in the cases of the FN+HP1 group of Example 3, FN+HP2 group of example 4 and EGF+HP1 group of Example 5, it was found not only that the cornea was regenerated but also that vacuolation and fibroblast growth can be suppressed. In addition, occurrence of inflammation was prevented.

In the case HP, FN and EGF were used together, as are in the cases of the EGF+FN+HP1 group of Example 6 and the HP1+HP2+FN+EGF group of Example 7, the corneal regeneration was observed. In addition, the thickness of the epithelium thereof was uniform. It was further confirmed that vacuolation and fibroblast growth were suppressed significantly. Furthermore, occurrence of inflammation can be prevented. In particular, the HP1+HP2+FN+EGF group of Example 7, it was demonstrated that the regenerated epithelium had a normal thickness, that vacuolation and fibroblast growth were rarely observed, and that a quite excellent corneal therapeutic effect was exhibited. As described, the corneal therapeutic effect can be enhanced by using HP, FN, and EGF together. It was successful to bring the state of the cornea after a surgical operation back closer to the state before operation.

We claim:

1. A method of preventing keratoleukoma comprising applying to the eye an amount of a hexapeptide effective to prevent keratoleukoma, wherein said hexapeptide is represented by the formula (I):

A-B-Pro-C-D-E        (I)

where

A is L- or D-arginine or lysine whose N-terminal amino group is deaminated, alkylated or acylated;

B is L- or D-arginine, lysine or histidine;

Pro is L- or D-proline;

C is L- or D-tyrosine, tryptophane, or phenylalanine;

D is L- or D-valine, isoleucine, or leucine having an amino group whose hydrogen atom may be substituted with an alkyl group having 1 to 4 carbon atoms; and E is L- or D-valine, isoleucine or leucine having a C-terminal carboxylic group which is unsubstituted or substituted with —COOR, —CH$_2$OR or —CONHR, where R represents a hydrogen atom or an alkyl group having 1 to 4 carbon atoms.

2. The method according to claim 1, wherein said hexapeptide is in a pharmacologically acceptable carrier.

3. The method according to claim 1, wherein said hexapeptide is selected from the group consisting of:

Desamino-Arg-Arg-Pro-Tyr-Ile-Leu-OH;

Desamino-Arg-Arg-Pro-Tyr-Ile-Leucinol;

Desamino-Arg-Lys-Pro-Tyr-Ile-Leu-NH$_2$;

Desamino-Arg-Arg-Pro-Trp-Ile-Leu-OEt;

N-acetyl-Arg-Arg-Pro-Tyr-Ile-Leu-OH;

N-acetyl-Arg-Arg-Pro-Tyr-Ile-Leucinol;

N-acetyl-Arg-Lys-Pro-Tyr-Ile-Leu-NH$_2$;

N-acetyl-Arg-Arg-Pro-Trp-Ile-Leu-OEt:

N-butyl-Arg-Arg-Pro-Tyr-Ile-Leu-OH;

N-butyl-Arg-Arg-Pro-Tyr-Ile-Leucinol;

N-butyl-Arg-Lys-Pro-Tyr-Ile-Leu-NH$_2$; and

N-butyl-Arg-Arg-Pro-Trp-Ile-Leu-OEt.

4. The method according to claim 2, wherein said hexapeptide is in the form of an eye drop containing said hexapeptide or its pharmacologically acceptable salt in an amount of 10 ng/ml to 100 ng/ml.

5. The method according to claim 2, wherein said hexapeptide is in the form of an eye ointment containing said hexapeptide or its pharmacologically acceptable salt in an amount of 10 ng/ml to 100 ng/ml.

* * * * *